United States Patent [19]
Bose et al.

[11] Patent Number: 5,248,589
[45] Date of Patent: Sep. 28, 1993

[54] SEPARATION OF CELLS AND BIOLOGICAL MACROMOLECULES BY FERRITIN CONJUGATES

[75] Inventors: Arijit Bose, Cambridge, Mass.; Srinivas V. Sonti, Narragansett, R.I.

[73] Assignee: Board of Governors for Higher Education, State of Rhode Island and Providence Plantations, Providence, R.I.

[21] Appl. No.: 821,703

[22] Filed: Jan. 16, 1992

Related U.S. Application Data

[63] Continuation-in-part of Ser. No. 659,578, Feb. 21, 1991, abandoned.

[51] Int. Cl.$^5$ .................... C12N 5/06; G01N 33/553
[52] U.S. Cl. ........................ 435/2; 209/214; 436/526; 436/801; 436/806; 436/828
[58] Field of Search ............ 435/2; 436/526, 801, 436/806, 828; 209/1, 4, 8, 39, 214, 223.1, 232; 252/62.56

[56] References Cited

U.S. PATENT DOCUMENTS

| | | | |
|---|---|---|---|
| 3,951,785 | 4/1976 | Kaiser et al. | 209/1 |
| 4,375,407 | 3/1983 | Kronick | 436/526 |
| 4,552,773 | 6/1984 | Molday | 436/526 X |

OTHER PUBLICATIONS

Templeton et al., "Ferritin-Conjugated Protein A," *FEBS Letters*, vol. 85, No. 1, (1978), pp. 95-98.

A. L. Lehninger, *Biochemistry*, 2nd Edition, Worth Publishers, Inc., N.Y., p. 59, (1970).

*Primary Examiner*—Esther L. Kepplinger
*Assistant Examiner*—Susan C. Wolski
*Attorney, Agent, or Firm*—Samuels, Gauthier & Stevens

[57] ABSTRACT

An Fc receptor protein conjugated with Ferritin binds to an exposed Fc region of an antibody to form a cell-/Ferritin complex. Magnetic particles are added to the medium and bind to the complex. The magnetic particles when bound to the complex significantly enhance the magnetic field gradient of the complex such that it may be separated magnetically from the medium.

3 Claims, 1 Drawing Sheet

SEPARATION OF CELLS AND BIOLOGICAL MACROMOLECULES BY FERRITIN CONJUGATES

CROSS REFERENCE TO RELATED APPLICATION

This application is a continuation-in-part of application Ser. No. 659,578 filed 21 February 1991 now abandoned.

FIELD OF THE INVENTION

This invention relates to the separation of biochemical species.

BACKGROUND AND BRIEF SUMMARY OF THE INVENTION

For both clinical therapy and biomedical research applications, there is a great need for a rapid and efficient technique for the separation and isolation of specific cell types from a mixture. For example, in the treatment of leukemia, cancerous lymphocytes can be separated from erythrocytes and other cell types in the blood. The healthy blood can then be transfused back into the patient's body. For treatment of childhood bone marrow cancer, diseased cells can be separated in vitro, and the normal cells can be put back into the body, avoiding the laborious (and often futile) process of looking for appropriate donors for a transplant. In AIDS patients, helper T cells which harbor the HIV virus within its genome need to be selectively removed, leaving behind B cells, erythrocytes and other healthy cells.

The use of magnetic particles for binding and separating target cells is known, see U.S. Pat. No. 4,965,007. In one technique, micron sized latex spheres with magnetic cores are coated with secondary antibodies that are specific to the target cells. The antibody bound target cells then bind to the microspheres and are separated from the mixture by a magnetic field. This method requires two antibodies and relies on three successful bindings—between latex/antibody, antibody/antibody and antibody/ target. For maximum efficiency, the antibodies on the latex should have their Fab regions exposed, a feature that has been particularly difficult to ensure. In addition, a new secondary antibody must be coated on the microspheres each time a new cell is targeted for removal. Furthermore, simultaneous removal of more than a single target from a mixture requires successful coating of multiple secondary antibodies on the microspheres.

An alternative method consists of coating functionalized silane layers on micron-sized magnetic particles. Ligands can then attach to the exposed functional group. Ligand-antiligand attraction and binding followed by exposure to a magnetic field gradient allows the antiligand to be preferentially separated. The ligand can be an antibody to a target cell, while the antiligand can be the target material.

The invention disclosed in the parent application was directed to an efficient and rapid method for sorting specific cell types from a mixture by using Fc receptor coated magnetic vesicles (liposomes). The invention was also useful for the separation of high valued biological macromolecules that appear in extremely low concentrations.

Briefly, the invention of the parent application comprised forming compartmented vesicles, preferably single compartment vesicles, having magnetic particles encapsulated therein. Embodied in the vesicle wall were Fc receptor proteins. The Fc domain of an antibody bound to the Fc site of the protein and the antibody bound to the surface antigen of a target cell. This complex of magnetic vesicle/Fc receptor/antibody/target cells was removed and each vesicle antibody-target cell was independently recovered.

The present invention deals with bioseparations using a ferritin-protein A conjugate. Ferritin, an iron storage protein, was disclosed in the parent application for a different purpose. There, the electron dense nature of ferritin was exploited to visualize by electron microscopy the location of protein-A on the vesicle walls.

In the present invention, we exploit the magnetic susceptibility of ferritin, rather than its electron dense property to effect a separation. Broadly, in the present invention, commercially available ferritin-protein A conjugates (Sigma Immunochemicals) are mixed into a solution containing antibody bound target cells. Because protein-A is an Fc receptor, the ferritin-protein-A conjugate binds to the exposed Fc domains of the antibodies, creating ferritinprotein A-antibody-target cell complexes. A ferrofluid containing a stable suspension of magnetic nanoparticles is then added to the solution. Because of the high magnetic field gradients of the ferrofluid particles, they atttach to the magnetically susceptible ferritin portion of the complex. The ferrofluid particle-target cell complex is then removed from solution by exposure to magnetized steel wool.

BRIEF DESCRIPTION OF THE DRAWINGS

Panels (a)–(g) of the figure are a schematic representation of a sequence of steps of a separation process of the invention.

DESCRIPTION OF THE PREFERRED EMBODIMENT(S)

Figure 1A:
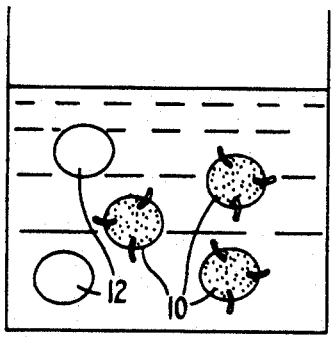
Figure 1B:
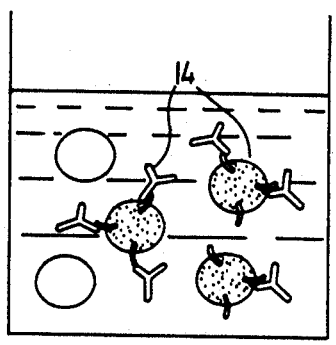
Figure 1C:
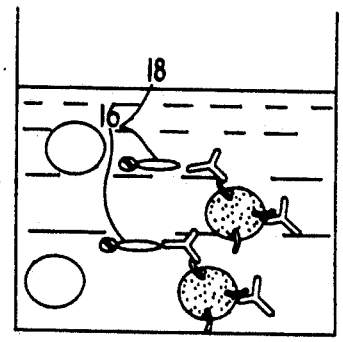
Figure 1D:
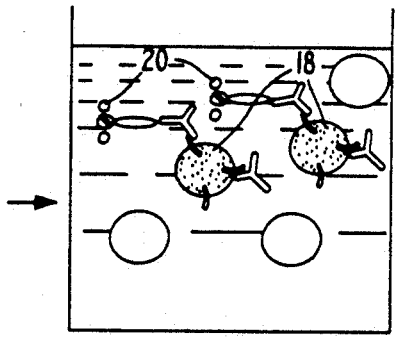
Figure 1E:
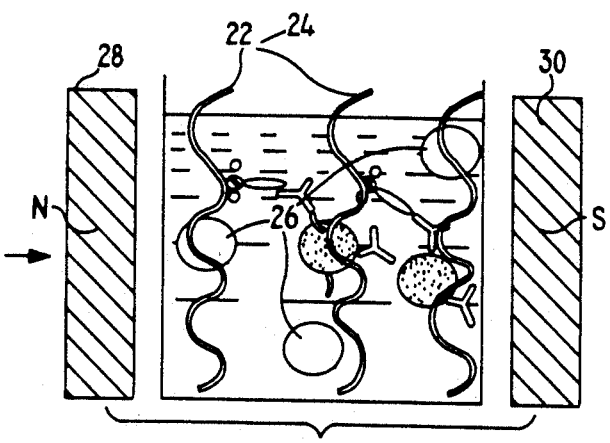
Figure 1F:
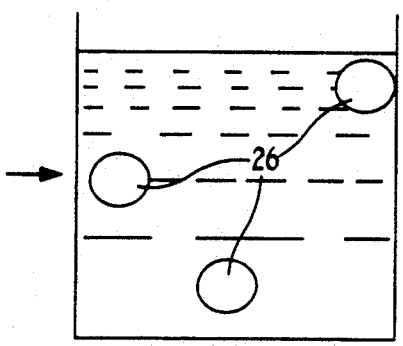
Figure 1G:
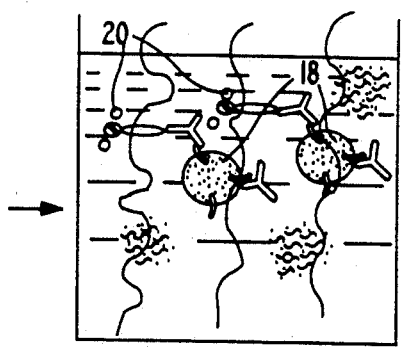

An immunomagnetic separation technique, using a cell mixture as an example, is outlined schematically in the figure. The cell mixture, step a, such as sheep and chicken red blood cells 10 and 12 respectively in 10 ml of phosphate buffered saline is exposed to monoclonal or polyclonal antibodies 14 (Sigma Immunochemicals S 8014 rabbit antisheep RBC antibody) which have specificity to one or more marker antigens on the sheep cell 10 membrane.

Through their Fab regions, these antibodies recognize and bind to the sheep cells only, step b.

Ferritin protein-A conjugates (Sigma Immunochemicals P 6530 Protein A-Ferritin) 16, step c, are added to the solution containing the cells and the antibodies. The Fc receptors (protein-A) on the conjugates bind to the Fc regions of the antibodies, creating cell/ferritin conjugate complexes 18.

To expedite the separation, a ferrofluid (Ferrofluids Corporation (EMG 705 or EMG 1111) of 10 nm diameter magnetic particles is added to the mixture, step d. There are magnetic field gradients present in the immediate vicinity of the particles. The ferritin conjugate/target cell complexes 18 attach to the magnetic particles 20 almost instantly.

Commonly available steel wool 22, 24 and 26, 25 $\mu$m in diameter, are placed in the solution, step e. A uniform magnetic field of $10^3$ gauss/cm is created by north and south magnetic poles 28 and 30. The complexes 18/20 bind to the steel wool 24 and 26.

The steel wool 22, 24 and 26 with the complexes 18/20 are removed, step f, and placed in 10 ml of phosphate buffered saline. The magnets 28 and 30 are removed causing the steel wool to demagnetize, step g. The steel wool is removed. The cells are recovered by adding NaCl until the salt concentration is greater than 1M. This breaks the bond between the antibodies and the cells. The cells are then recovered by centrifuging.

Although described with reference to the separation of sheep red blood cells from a mixture of sheep and chicken red blood cells, the invention embodies the acquisition of other cells and including other biological macromolecules, etc.

The foregoing description has been limited to a specific embodiment of the invention. It will be apparent, however, that variations and modifications can be made to the invention, with the attainment of some or all of the advantages of the invention. Therefore, it is the object of the appended claims to cover all such variations and modifications as come within the true spirit and scope of the invention.

Having described my invention, what I now claim is:

1. A method for separating target cells from untargeted cells wherein the cells are in a liquid medium which comprises:

adding antibody specific for the target cell to the medium wherein the antibodies bind to antigens of the target cells through their Fab regions;

adding an Fc receptor protein conjugated with Ferritin to the medium wherein the Fc receptor protein specifically binds to the exposed Fc regions of the antibody to form a cell/Ferritin complex;

adding a ferrofluid to the medium, the ferrofluid including magnetic particles which magnetic particles attach to the complex;

adding steel wool to the medium;

applying a defined magnetic field to the medium to produce magnetized steel;

concentrating the complex within the defined magnetic field by binding of the complex to the magnetized steel wool;

separating the concentrated complex from the untargeted cells; and recovering the target cells.

2. The method of claim 1 wherein the Fc receptor protein in Protein-A.

3. The method of claim 1 which includes:

disassociating the components of the complex after the complex has been separated from the liquid medium.

* * * * *